United States Patent
Lee et al.

(10) Patent No.: US 10,395,767 B2
(45) Date of Patent: *Aug. 27, 2019

(54) METHOD AND APPARATUS FOR MANAGING MEDICAL DATA

(71) Applicant: SAMSUNG ELECTRONICS CO., LTD., Suwon-si (KR)

(72) Inventors: Woong Lee, Suwon-si (KR); Nasir Desai, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 68 days.

This patent is subject to a terminal disclaimer.

(21) Appl. No.: 15/413,759

(22) Filed: Jan. 24, 2017

(65) Prior Publication Data

US 2017/0132381 A1    May 11, 2017

Related U.S. Application Data

(63) Continuation of application No. 14/312,895, filed on Jun. 24, 2014, now Pat. No. 9,582,840.

(30) Foreign Application Priority Data

Jun. 24, 2013    (KR) .................... 10-2013-0072705

(51) Int. Cl.
*G06F 11/07*    (2006.01)
*G16H 40/20*    (2018.01)
(Continued)

(52) U.S. Cl.
CPC ......... *G16H 40/20* (2018.01); *G06F 11/0748* (2013.01); *G06F 11/3438* (2013.01);
(Continued)

(58) Field of Classification Search
None
See application file for complete search history.

(56) References Cited

U.S. PATENT DOCUMENTS 6,381,557 B1 * 4/2002 Babula .................. G16H 40/40
                                                                702/183
2006/0085525 A1    4/2006 Beck
(Continued)

FOREIGN PATENT DOCUMENTS

JP        2561561 B2      7/1992
JP     2009291308 A     12/2009
(Continued)

OTHER PUBLICATIONS

Notice of Allowance dated Feb. 3, 2015 issued by the Korean Intellectual Property Office in counterpart Korean Application No. 10-2013-0072705.

(Continued)

*Primary Examiner* — Yolanda L Wilson
(74) *Attorney, Agent, or Firm* — Sughrue Mion, PLLC

(57) ABSTRACT

Provided are a method and apparatus for managing medical data. The method includes sensing an error event of a medical diagnosis device; obtaining image data by capturing images of a user input of the medical diagnosis device with respect to a first period of time associated with a time that the error event is sensed; obtaining log data corresponding to the image data, from a console device for controlling the medical diagnosis device; and transmitting the image data and the log data to an external server.

30 Claims, 10 Drawing Sheets

(51) Int. Cl.
  *G06F 11/34* (2006.01)
  *G16H 40/63* (2018.01)
  *G06Q 50/24* (2012.01)
  *G06F 19/00* (2018.01)
  *H04N 7/18* (2006.01)
  *G16H 40/40* (2018.01)

(52) U.S. Cl.
  CPC ........ *G06F 19/321* (2013.01); *G06F 19/3418* (2013.01); *G06Q 50/24* (2013.01); *G16H 40/63* (2018.01); *H04N 7/183* (2013.01); *G16H 40/40* (2018.01); *H04N 7/18* (2013.01)

(56) References Cited

U.S. PATENT DOCUMENTS

| | | | |
|---|---|---|---|
| 2006/0242092 A1* | 10/2006 | Rometsch | G06F 11/3419 706/15 |
| 2007/0018784 A1 | 1/2007 | Yoon et al. | |
| 2007/0214017 A1 | 9/2007 | Profio et al. | |
| 2009/0210754 A1* | 8/2009 | Sekiguchi | G06F 11/327 714/57 |
| 2010/0245583 A1 | 9/2010 | Harel | |
| 2013/0258074 A1 | 10/2013 | Zhai | |
| 2013/0304489 A1* | 11/2013 | Miller | G06Q 10/20 705/2 |
| 2014/0149967 A1 | 5/2014 | Deshpande | |
| 2014/0253703 A1 | 9/2014 | King | |
| 2015/0033073 A1 | 1/2015 | Yang | |
| 2015/0062328 A1 | 3/2015 | Lauffer | |

FOREIGN PATENT DOCUMENTS

| | | |
|---|---|---|
| KR | 10-0598588 B1 | 7/2006 |
| KR | 1020070011086 A | 1/2007 |
| KR | 1020090035839 A | 4/2009 |
| KR | 1020100137147 A | 12/2010 |
| KR | 10-2011-0064384 A | 6/2011 |
| KR | 101234791 B1 | 3/2013 |
| KR | 101241582 B1 | 3/2013 |

OTHER PUBLICATIONS

Office Action dated Aug. 18, 2014 issued by the Korean Intellectual Property Office in counterpart Korean Application No. 10-2013-0072705.

Communication dated Oct. 2, 2014, issued by the International Searching Authority in counterpart International Application No. PCT/KR2014/005511.

Communication dated Feb. 3, 2015 issued by Korean Intellectual Property Office in counterpart Korean Application No. 10-2013-0072705.

Non-Final Office Action dated Jul. 1, 2016 in U.S. Appl. No. 14/312,895.

Notice of Allowance dated Oct. 17, 2016 in U.S. Appl. No. 14/312,895.

Communication dated Feb. 9, 2017, issued by the European Patent Office in counterpart European Patent Application No. 14817641.5.

\* cited by examiner

METHOD AND APPARATUS FOR MANAGING MEDICAL DATA

CROSS-REFERENCE TO RELATED PATENT APPLICATION

This application is a Continuation of U.S. patent application Ser. No. 14/312,895, filed on Jun. 24, 2014 in the U.S. Patent and Trademark Office, which claims priority from Korean Patent Application No. 10-2013-0072705, filed on Jun. 24, 2013, in the Korean Intellectual Property Office, the disclosure of which is incorporated herein in its entirety by reference.

BACKGROUND

1. Field

Exemplary embodiments relate to a method and apparatus for obtaining, managing, and transmitting medical data.

2. Description of the Related Art

A medical diagnosis system includes a large number of parts and components for processing clinical information and diagnosing an object. As such, a user who manipulates a medical diagnosis system needs high-level skills and knowledge.

If a user makes an error when manipulating a medical diagnosis system or a hardware/software problem inside the system exists, an error may be generated during the operation of the medical diagnosis system. In other words, the operation of a medical diagnosis system may be interrupted or the function of the system may temporarily deteriorate due to an unexpected problem.

Typically, in order to solve the above problem, log information stored in a console device of a medical diagnosis system is analyzed, or a debugging process using a debugging board is performed.

SUMMARY

Exemplary embodiments provide a method and apparatus for obtaining, managing, and transmitting medical data.

Exemplary embodiments may also provide a computer-readable recording medium having recorded thereon a computer program for executing the method.

According to an aspect of an exemplary embodiment, there is provided a method of managing medical data, performed by a medical data management apparatus, the method including sensing an error event of a medical diagnosis device; obtaining image data by capturing images of a user input unit of the medical diagnosis device with respect to a first period of time associated with a time that the error event is sensed; obtaining log data corresponding to the image data, from a console device for controlling the medical diagnosis device; and transmitting the image data and the log data to an external server.

The obtaining of the image data may include capturing images of the user input unit of the medical diagnosis device; and extracting images corresponding to the first period of time, from the captured images.

The obtaining of the log data may include transmitting information about the first period of time to the console device; and receiving log data matched to the first period of time, from the console device.

The image data and the log data may correspond to each other based on the first period of time.

The method may further include obtaining image data corresponding to a second period of time after the error event is sensed, from the images of the user input unit; obtaining log data corresponding to the second period of time, from the console device; and transmitting the image data corresponding to the second period of time and the log data corresponding to the second period of time, to the external server.

The method may further include receiving a further transmission request from the external server; further obtaining image data and log data corresponding to a period of time according to the further transmission request; and transmitting the further obtained image data and the further obtained log data to the external server.

The method may further include obtaining sound data of an operating room where the medical diagnosis device is located, with respect to the first period of time, and the transmitting may include transmitting the image data, the log data, and the sound data.

The sensing may include receiving an error event notification signal from the medical diagnosis device.

The sensing may include executing at least one of a pattern recognition algorithm, a gesture recognition algorithm, and a color detection algorithm on the images of the user input unit.

The transmitting may include transmitting information about one of the algorithms, the executing of which results in the error event being sensed.

The log data may include at least one of a history of using the console device, user information of the console device, software information of the console device, setup information of the console device, system information of the console device, and hospital information about a hospital where the medical data management apparatus is located.

The method may further include obtaining room image data by capturing images of inside an operating room where the medical diagnosis device is located, with respect to the first period of time, and the transmitting may include transmitting the image data, the log data, and the room image data.

The method may further include setting an area for displaying the image data on a display unit; and providing the image data on the set area.

The image data may be obtained by an image capturing unit shielded from the medical diagnosis device.

The image data may be obtained by at least one of an ultra-high-speed camera, a wide-viewing-angle camera, and a high-definition (HD) camera.

According to an aspect of another exemplary embodiment, there is provided a medical data management apparatus including an image capturing unit for capturing images of a user input unit of a medical diagnosis device; an event sensing unit for sensing an error event of the medical diagnosis device; an image data management unit for obtaining image data by capturing images of the user input unit of the medical diagnosis device with respect to a first period of time associated with a time that the error event is sensed; a log data management unit for obtaining log data corresponding to the image data, from a console device for controlling the medical diagnosis device; and a communication unit for transmitting the image data and the log data to an external server.

According to an aspect of another exemplary embodiment, there is provided a non-transitory computer-readable recording medium having recorded thereon a computer program for executing the above method.

BRIEF DESCRIPTION OF THE DRAWINGS

The above and other features and advantages will become more apparent by describing in detail exemplary embodiments with reference to the attached drawings in which.

DETAILED DESCRIPTION OF THE EXEMPLARY EMBODIMENTS

Figure 1:
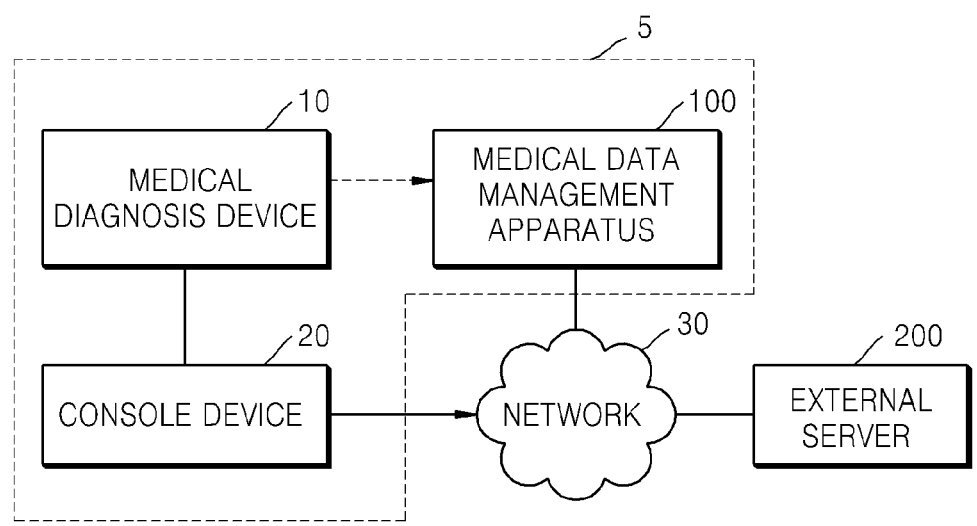
FIG. 1 is a schematic diagram showing correlations between a medical data management apparatus, a medical diagnosis device, a console device, and an external server, according to an exemplary embodiment.

All terms including descriptive or technical terms which are used herein should be construed as having meanings that are known to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" may be embodied as, but not limited to, software or a hardware component, such as a field programmable gate array (FPGA) or an application specific integrated circuit (ASIC). However, a unit may advantageously be configured to reside on an addressable storage medium and configured to execute one or more processors. Thus, a unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and units may be combined into fewer components and units or further separated into additional components and units.

Throughout the specification, an "image" may mean multi-dimensional data including discrete image elements (e.g., pixels of a two-dimensional (2D) image and voxels of a three-dimensional (3D) image). For example, the image may include a medical image of an object which is obtained by using an X-ray diagnosis system, a computed tomography (CT) diagnosis system, a magnetic resonance imaging (MRI) diagnosis system, an ultrasound diagnosis system, or another medical diagnosis system.

Also, throughout the specification, an "object" may include a human, an animal, or a part of a human or animal. For example, the object may include organs such as liver, heart, womb, brain, breast, abdomen, or the like, or a blood vessel. Also, the object may include a phantom. The phantom means a material having a volume that is very close to a density and effective atomic number of an organism, and may include a sphere phantom having a characteristic similar to a physical body.

Throughout the specification, a "user" may be, but is not limited thereto, a medical expert including a doctor, a nurse, a medical laboratory technologist, a medial image expert, a radiologist, and a technician who repairs a medical apparatus.

Exemplary embodiments will now be described more fully with reference to the accompanying drawings. The exemplary embodiments may, however, be embodied in many different forms and should not be construed as being limited to the exemplary embodiments set forth herein; rather, these exemplary embodiments are provided so that this disclosure will be thorough and complete, and will fully convey the inventive concept to those of ordinary skill in the art. In the following description, well-known functions or constructions are not described in detail since they would obscure the exemplary embodiments with unnecessary detail. Throughout the specification, like reference numerals in the drawings denote like elements.

As used herein, the term "and/or" includes any and all combinations of one or more of the associated listed items. Expressions such as "at least one of," when preceding a list of elements, modify the entire list of elements and do not modify the individual elements of the list.

FIG. 1 is a schematic diagram showing correlations between a medical data management apparatus 100, a medical diagnosis device 10, a console device 20, and an external server 200, according to an exemplary embodiment. In FIG. 1, the medical data management apparatus 100 may be connected to the medical diagnosis device 10, the console device 20, and the external server 200. The medical diagnosis device 10, the console device 20, and the medical data management apparatus 100 may be connected to each other so as to form a medical diagnosis system 5.

The medical diagnosis device 10 may refer to a device for performing medical diagnosis on an object. A user of the medical diagnosis device 10 may control various components of the medical diagnosis device 10 by manipulating a user input unit included in the medical diagnosis device 10. The medical diagnosis device 10 may diagnose an object and may generate medical images. Also, the medical diagnosis device 10 may display and output the generated medical images.

The medical diagnosis device 10 may include at least one of an MRI diagnosis device, an X-ray diagnosis device, a CT diagnosis device, and an ultrasound diagnosis device. However, the above-mentioned diagnosis devices are merely examples, and the medical diagnosis device 10 may include diagnosis devices according to various modalities as well as the above diagnosis devices.

The console device 20 may refer to a device for controlling and managing the medical diagnosis device 10. The console device 20 may receive and analyze system information of the medical diagnosis device 10, and may monitor whether the medical diagnosis device 10 operates without an error. Also, the console device 20 may obtain and store the system information of the medical diagnosis device 10.

The console device 20 may be separate from the medical diagnosis device 10 and may be located in a console room. A user of the console device 20 may monitor and manage the medical diagnosis device 10 by manipulating the console device 20 in the console room.

The medical data management apparatus 100 obtains and manages medical data. The "medical data" may refer to data obtained by the medical data management apparatus 100, and may include image data and log data. The image data and the log data will be described in detail below.

The medical data management apparatus 100 may obtain the image data from the above-described medical diagnosis device 10, and may obtain the log data from the console device 20. Also, the medical data management apparatus 100 may communicate with and may transmit the image data and the log data to the external server 200. The medical data management apparatus 100 may be connected to the external server 200 and the console device 20 via a network 30 by wire or wirelessly.

The "image data" may refer to images of the user input unit of the medical diagnosis device 10. In other words, the medical data management apparatus 100 may capture images of the user input unit of the medical diagnosis device 10, and may obtain the captured images of the user input unit as the image data.

The "log data" may refer to the system information of the medical diagnosis device 10. In other words, the medical data management apparatus 100 may receive the system information obtained by the console device 20 from the medical diagnosis device 10, and may manage the system information as the log data. The log data may include backup data for system restoration when the medical diagnosis device 10 malfunctions.

The external server 200 is connected to the medical data management apparatus 100 and controls the medical diagnosis system 5. The external server 200 may analyze the medical data received from the medical data management apparatus 100, i.e., the image data and the log data, and may control the medical diagnosis device 10, the console device 20, and the medical data management apparatus 100.

For example, the external server 200 may perform an operation for correcting a malfunction of the medical diagnosis device 10, by analyzing the log data of the medical diagnosis device 10. The external server 200 may include a service center server or a management center server of the medical diagnosis system 5.

Figure 2:
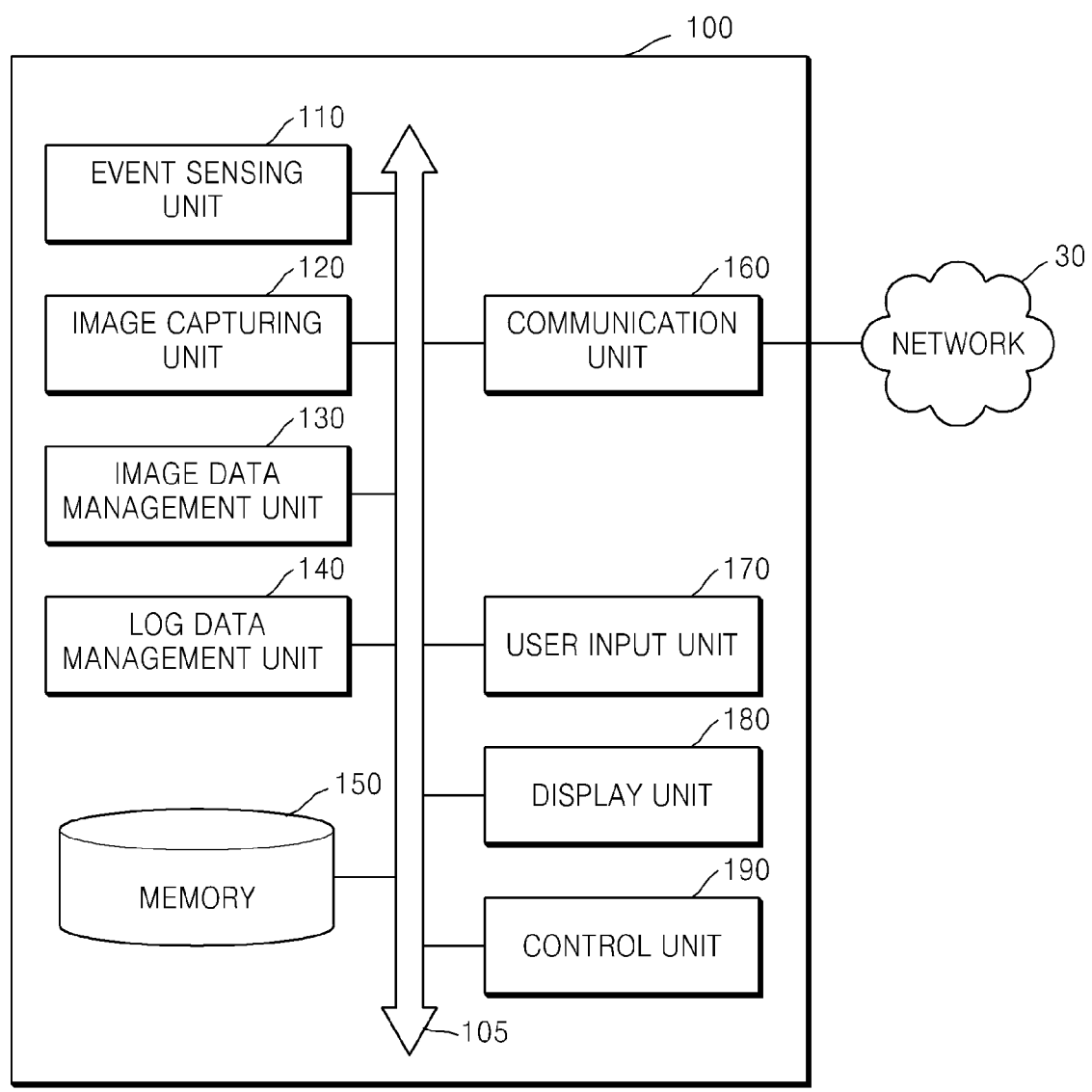
FIG. 2 is a block diagram of a medical data management apparatus according to an exemplary embodiment.

FIG. 2 is a block diagram of the medical data management apparatus 100 according to an exemplary embodiment. In other words, the medical data management apparatus 100 may further include general components in addition to those illustrated in FIG. 2, or may not include some of the components illustrated in FIG. 2. Accordingly, the medical data management apparatus 100 is not limited to the illustration and description of FIG. 2.

The medical data management apparatus 100 may include an event sensing unit 110 (e.g., an event sensor), an image capturing unit 120 (e.g., an image capturer), an image data management unit 130 (e.g., an image data manager), a log data management unit 140 (e.g., a log data manager), a memory 150, a communication unit 160 (e.g., a communicator), a user input unit 170 (e.g., a user input), a display unit 180 (e.g., a display), and a control unit 190 (e.g., a controller). The components of the medical data management apparatus 100 illustrated in FIG. 2 may be connected to each other and may exchange data via a system bus 105. Each of the components will now be described in detail.

The event sensing unit 110 senses an error event of the medical diagnosis device 10. In other words, the event sensing unit 110 may obtain information about an error of the medical diagnosis device 10. The "error event" may refer to an event where an unexpected result is generated in the medical diagnosis device 10 due to a malfunction or a system error.

For example, an operation of the medical diagnosis device 10 may be interrupted due to an incorrect manipulation by the user. Alternatively, the medical diagnosis device 10 may not normally operate due to a failure or a crash of hardware or software. As another example, some or all functions of the medical diagnosis device 10 may be interrupted due to a power supply or circuit error. In addition to the above-described examples, the "error event" may refer to all unexpected results generated in the medical diagnosis device 10.

As such, the event sensing unit 110 may sense an error event by using various methods. For example, the event sensing unit 110 may receive an error event notification signal from the medical diagnosis device 10. The error event notification signal may be a signal generated by the medical diagnosis device 10 when an error event is generated.

As another example, the event sensing unit 110 may sense whether an error event is generated in the medical diagnosis device 10, by cyclically exchanging check data with the medical diagnosis device 10. In other words, if check data is not received from the medical diagnosis device 10, the event sensing unit 110 may recognize that an error event is generated in the medical diagnosis device 10.

As another example, the event sensing unit 110 may sense an error event by using a software method using various algorithms. In other words, the event sensing unit 110 may obtain captured images of a user input unit of the medical diagnosis device 10 or captured images of an operating room where the medical diagnosis device 10 is located, and may apply one or more algorithms to the obtained images. The event sensing unit 110 may use various types of algorithms such as a pattern recognition algorithm, a gesture recognition algorithm, and a color detection algorithm.

In more detail, the event sensing unit 110 may detect an unexpected pattern that is different from a predetermined pattern, on the captured images of the user input unit of the medical diagnosis device 10. Likewise, the event sensing unit 110 may detect an abnormal gesture or operation performed with respect to the captured images of the user input unit. Lastly, the event sensing unit 110 may sense generation of an error event based on color variations on the images.

As another example, the event sensing unit 110 may sense generation of an error event according to a user input received by the user input unit 170. In other words, a user may interrupt an operation of the medical diagnosis device 10 or the medical data management apparatus 100 according to a necessity. As such, the event sensing unit 110 may receive a user input for a system interrupt via the user input unit 170, and may recognize that an error event is generated, based on the user input.

As described above, the event sensing unit 110 may sense an error event actively, or passively by using a user input.

Also, in addition to the above-described examples, the event sensing unit 110 may sense an error event by using other various methods.

The image capturing unit 120 captures images of the user input unit of the medical diagnosis device 10. The image capturing unit 120 may capture images of the medical diagnosis device 10 by using an imaging element such as a camera. The image capturing unit 120 may include various types of imaging elements such as an ultra-high-speed camera, a wide-viewing-angle camera, and a high-definition (HD) camera. Also, the image capturing unit 120 may include a plurality of imaging elements.

The image capturing unit 120 may continuously monitor a user's manipulation on the medical diagnosis device 10 by capturing images of the user input unit of the medical diagnosis device 10. The medical diagnosis device 10 may include one or more elements for receiving from a user an input for manipulating the medical diagnosis device 10. For example, the medical diagnosis device 10 may include various input elements, e.g., a keyboard, a keypad, a mouse, a touch pad, a touch panel, a touch screen, knob buttons, a jog switch, and a track ball, as the user input unit.

As such, the image capturing unit 120 may be located near the user input unit of the medical diagnosis device 10, and may capture images of the user input unit. Examples wherein images of the user input unit of the medical diagnosis device 10 are captured according to various types of modalities will be described below with reference to FIGS. 9 through 12.

The image capturing unit 120 may capture images of the operating room where the medical diagnosis device 10 is located. In other words, the image capturing unit 120 may capture images of inside the operating room and thus may generate room image data. If images of the user input unit are not easily captured due to motion of a user or a body part of the user, the medical data management apparatus 100 may additionally use the captured images of the inside of the operating room.

Also, the image capturing unit 120 may capture images of an object in the operating room. In other words, the image capturing unit 120 may be located near a location where the medical diagnosis device 10 diagnoses an object, e.g., a diagnosis table, a cradle, or a diagnosis chair in the operating room, and may capture images of the object during medical diagnosis. Then, the image capturing unit 120 may generate object image data including the captured images of the object.

The image capturing unit 120 may store the captured images of the user input unit of the medical diagnosis device 10, the captured images of the operating room, or the captured images of the object in the memory 150. The image capturing unit 120 may store the captured images in the memory 150 together with time information about times when the images are captured.

Also, the image capturing unit 120 may be shielded from the medical diagnosis device 10 in the operating room. In other words, the medical diagnosis device 10 such as an MRI diagnosis device or a CT diagnosis device irradiates a magnetic field or an X-ray. As such, the image capturing unit 120 may be located in the operating room while being shielded from a magnetic field, a radio frequency (RF) signal, or an X-ray generated by the medical diagnosis device 10.

The image data management unit 130 obtains and manages some or all of image data including the images captured by the image capturing unit 120. In other words, the image data management unit 130 may manage the captured images of the user input unit of the medical diagnosis device 10 or the captured images of the operating room.

In more detail, the image data management unit 130 may extract the image data corresponding to a certain period of time of the image data captured by the image capturing unit 120 and stored in the memory 150. The period of time may refer to a certain period of time before and/or after the event sensing unit 110 senses the error event. For example, the period of time may be a period of time from 5 minutes before the error event is generated, till 10 minutes after the error event is generated. The period of time may directly precede, overlap with, or come directly after the error event.

Also, the image data management unit 130 may further obtain the image data corresponding to a certain period of time according to a further transmission request received from the external server 200. In other words, if a request for the image data corresponding to a 10 minute time period before the error event is generated is received from the external server 200, the image data management unit 130 may obtain the image data corresponding to the above period of time, from the memory 150.

The log data management unit 140 obtains and manages log data from the console device 20. In other words, the log data management unit 140 may receive the log data including system information of the medical diagnosis device 10, from the console device 20, and may store the log data in the memory 150.

Also, the log data management unit 140 may obtain the log data corresponding to a certain period of time. The log data management unit 140 may transmit information about the certain period of time to the console device 20, and may receive the log data matched to the period of time, from the console device 20.

Alternatively, the log data management unit 140 may obtain some or all of the log data stored in the memory 150. In other words, the log data management unit 140 may extract the log data corresponding to a certain period of time, from the log data stored in the memory 150.

Furthermore, the log data management unit 140 may further obtain the log data corresponding to a certain period of time according to the further transmission request received from the external server 200. In other words, the log data management unit 140 may obtain the log data corresponding to a certain period of time before and/or after the error event is sensed.

The log data may include at least one of a history of using the console device 20, user information about a user who is logged in the console device 20, software information about software installed in the console device 20, hardware/software setup information of the console device 20, system information of the console device 20, and hospital information about a hospital where the medical data management apparatus 100 is located.

The memory 150 may store data and information input/output to the medical data management apparatus 100. For example, the memory 150 may store the image data captured by the image capturing unit 120, and may store the log data received by the log data management unit 140 from the console device 20. Also, the memory 150 may store various types of program data or algorithm data executable by the medical data management apparatus 100.

The memory 150 may include at least one of a flash memory type storage medium, a hard disk type storage medium, a multimedia card micro type storage medium, a card-type memory (e.g., a security digital (SD) or extreme digital (XD) memory), a random access memory (RAM), a static random access memory (SRAM), a read-only memory (SRAM), an electrically erasable programmable read-only memory (EEPROM), a programmable read-only memory (PROM), a magnetic memory, a magnetic disk, and an optical disk. Also, the medical data management apparatus 100 may operate a web storage or a cloud server, which performs the functions of the memory 150 on the internet.

The communication unit 160 is connected to the network 30 by wire or wirelessly and communicates with an external device or server. The communication unit 160 may exchange data with a hospital server connected via a picture archiving and communication system (PACS), the external server 200, the medical diagnosis device 10, and the console device 20. Also, the communication unit 160 may perform data communications according to the digital imaging and communications in medicine (DICOM) standard.

The communication unit 160 may transmit and receive the image data and the log data, or may receive a data request signal or a device control command, via the network 30. Also, the communication unit 160 may transmit and receive medical images captured by a device other than the medical diagnosis device 10.

Also, the communication unit 160 may receive a result of diagnosing the object from the medical diagnosis device 10 as scan data, that is, data about medical images. The communication unit 160 may receive the scan data from the medical diagnosis device 10, and may transmit the scan data to the external server 200 in addition to the image data and the log data.

As another example, the communication unit 160 may transmit to the external server 200 information about a method of sensing generation of the error event by the event sensing unit 110. In other words, if the event sensing unit 110 senses the error event by receiving an error event notification signal or by applying an algorithm to the image data, information about each method may be transmitted to the external server 200. As such, the external server 200 may check how the medical data management apparatus 100 has sensed the error event.

The communication unit 160 may include one or more components for enabling communications via the network 30, e.g., a short-distance communication module, a wire communication module, and a mobile communication module.

The short-distance communication module refers to a module for short-distance communications within a certain distance. A short-distance communication technology according to an exemplary embodiment may include, but is not limited to, wireless local area network (WLAN), wireless fidelity (Wi-Fi), Bluetooth, ZigBee, Wi-Fi direct (WFD), ultra wideband (UWB), infrared data association (IrDA), Bluetooth low energy (BLE), or near field communication (NFC).

The wire communication module refers to a module for communications using an electrical signal or an optical signal. A wire communication technology according to an exemplary embodiment may include, for example, a pair cable, a coaxial cable, an optical fiber cable, or an Ethernet cable.

The mobile communication module transmits and receives a wireless signal to and from at least one of a base station, an external terminal, and a server in a mobile communication network. Here, the wireless signal may include various types of data according to transmission and reception of a voice call signal, a video call signal, or a text/multimedia message.

The user input unit 170 refers to an element for allowing a user (e.g., a sonographer) to input data for controlling the medical data management apparatus 100. For example, the user input unit 170 may include, but is not limited to, a keyboard, a keypad, a mouse, a dome switch, a track ball, a touch pad (e.g., a capacitive overlay type, a resistive overlay type, an infrared beam type, a surface acoustic wave type, an integral strain gauge type, or a piezoelectric type), a jog wheel, or a jog switch. Particularly, if a touch pad forms a layer structure together with a display panel, the layer structure may be referred to as a touch screen.

The user input unit 170 may detect a proximity touch as well as a real touch. The user input unit 170 may sense a touch input (e.g., a touch & hold, a tap, a double tap, or a flick) on an image output by the display unit 180. Also, the user input unit 170 may sense a drag input from a point where a touch input is sensed. Furthermore, the user input unit 170 may sense a multi-touch input (e.g., a pinch) on at least two points.

The user input unit 170 may receive a user input for setting an area for displaying the image data on the display unit 180.

The display unit 180 displays and outputs information processed by the medical data management apparatus 100. For example, the display unit 180 may output a plurality of image data captured by the image capturing unit 120. The display unit 180 may display and output the image data on the area set by the user.

If the display unit 180 and a touchpad form a touch screen in a layer structure, the display unit 180 may be used as an input apparatus as well as an output apparatus. The display unit 180 may include at least one of a liquid crystal display (LCD), a thin film transistor LCD (TFT LCD), an organic light-emitting diode (OLED), a flexible display, a three-dimensional (3D) display, and an electrophoretic display. The medical data management apparatus 100 may include two or more display units 180.

The control unit 190 controls all operations of the medical data management apparatus 100. In other words, the control unit 190 may control the image capturing unit 120 to store captured images in the memory 150, or may control the image data management unit 130 and the log data management unit 140 to extract data stored in the memory 150. Alternatively, the control unit 190 may control the communication unit 160 to exchange data by performing communications via the network 30.

Although not shown in FIG. 2, the medical data management apparatus 100 may further include a sound data management unit (not shown). The sound data management unit may record sound generated in the operating room, and may store the recorded sound as sound data in the memory 150. Like the image data management unit 130 and the log data management unit 140, the sound data management unit may extract sound data corresponding to a certain period of time. The communication unit 160 according to an exemplary embodiment may transmit the sound data to the external server 200 in addition to the image data and the log data.

Figure 3:
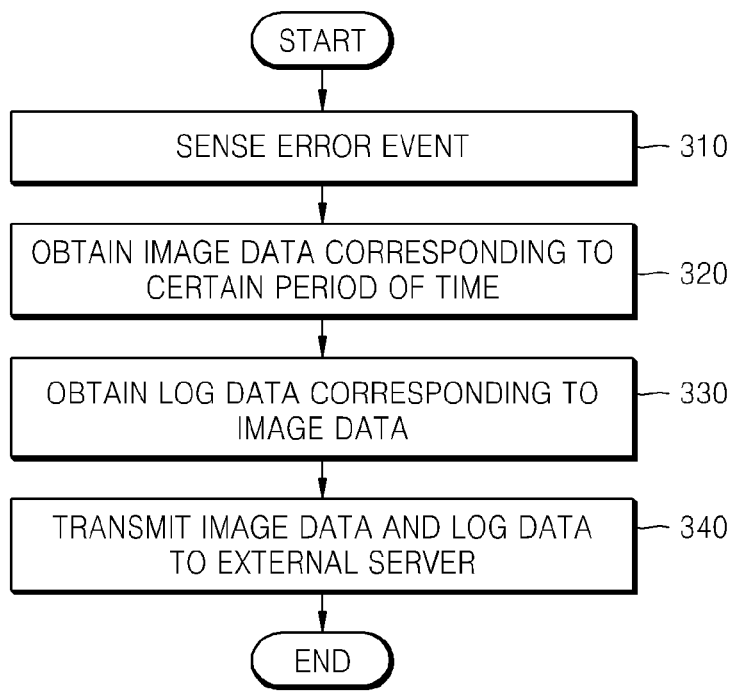
FIG. 3 is a flowchart of a method of managing medical data, according to an exemplary embodiment.

FIG. 3 is a flowchart of a method of managing medical data, according to an exemplary embodiment. The method of FIG. 3 includes operations performed by the components included in the medical data management apparatus 100 described above in relation to FIGS. 1 and 2. Accordingly, although not described below, the descriptions provided above in relation to FIGS. 1 and 2 are also applied to the method of FIG. 3.

In operation 310, the medical data management apparatus 100 senses an error event of the medical diagnosis device 10. In other words, the medical data management apparatus 100 may sense generation of an unexpected result due to a malfunction of the medical diagnosis device 10.

As described above in relation to FIG. 2, the medical data management apparatus 100 may sense generation of an error event by receiving an error event notification signal from the medical diagnosis device 10, or by analyzing image data.

In operation 320, the medical data management apparatus 100 obtains the image data corresponding to a certain period of time. In other words, the medical data management apparatus 100 captures and stores images of a user input unit of the medical diagnosis device 10 by using the image capturing unit 120. In operation 320, the medical data management apparatus 100 may obtain the image data corresponding to a period of time determined in relation to generation of the error event.

The medical data management apparatus 100 may obtain the image data corresponding to a certain period of time before the error event is generated. In other words, the medical data management apparatus 100 may extract the image data corresponding to a certain period of time before the error event is generated, from the accumulatively stored image data.

For example, the medical data management apparatus 100 may extract the image data corresponding to a 5 minute time period before the error event is generated. The period of time of the image data obtained by the medical data management apparatus 100 may be a predetermined period of time, and may be adjusted according to a user input.

In operation 330, the medical data management apparatus 100 obtains log data corresponding to the image data. In other words, the medical data management apparatus 100 obtains the log data corresponding to the period of time of the image data obtained in operation 320.

The medical data management apparatus 100 may transmit information about the period of time of the image data to the console device 20, and may receive the log data matched to the period of time, from the console device 20.

In operations 320 and 330, the medical data management apparatus 100 may obtain the image data and the log data matched to each other with respect to the same period of time. The matched image data and the log data may be synchronized with each other based on information about the period of time.

In operation 340, the medical data management apparatus 100 transmits the image data and the log data to the external server 200. In other words, the medical data management apparatus 100 may transmit medical data obtained in operations 320 and 330 (i.e., the image data and the log data) to the external server 200.

The medical data management apparatus 100 may transmit the medical data to the external server 200, and may receive feedback information from the external server 200 including a service center server. As such, the medical data management apparatus 100 may not perform a debugging process on the medical diagnosis device 10. In other words, the debugging process may cause an overload of the medical diagnosis device 10 and the console device 20 and thus may reduce a processing speed, and the medical data management apparatus 100 may solve the above problem.

In more detail, the external server 200 that has received the medical data may analyze the image data as well as the log data. In other words, by solving a systematic problem while checking whether a user's manipulation is correct, the external server 200 may easily check a problem of the error event generated in the medical diagnosis device 10 and the console device 20.

Figure 4:
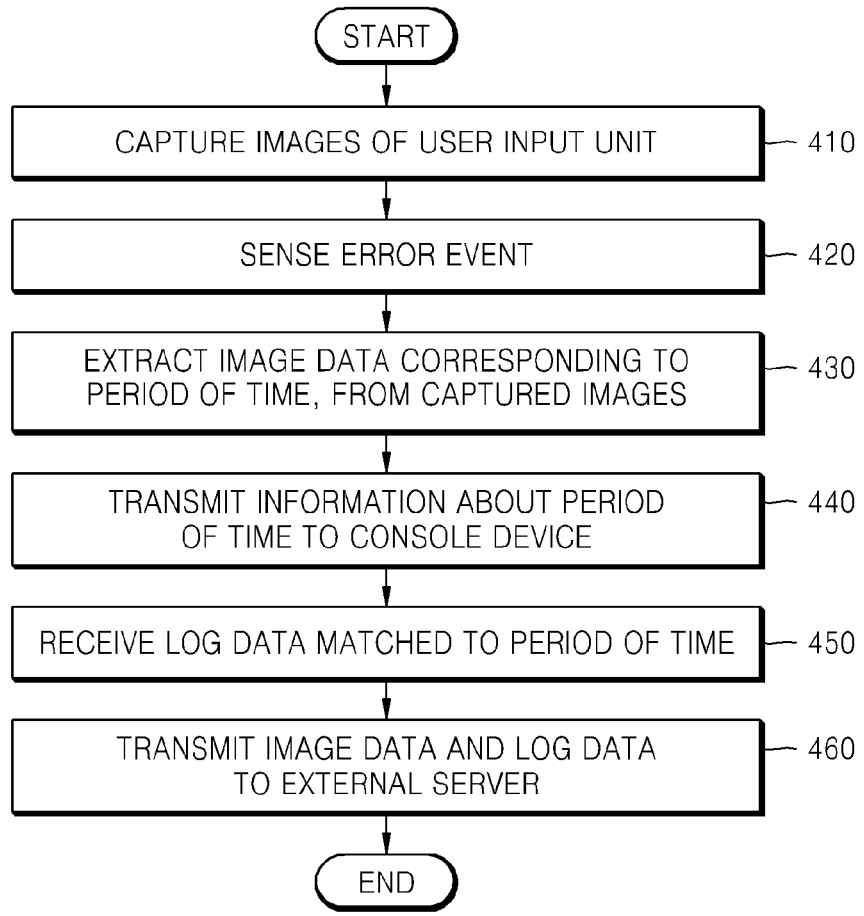
FIG. 4 is a flowchart of a method of managing medical data, according to an exemplary embodiment.

FIG. 4 is a flowchart of a method of managing medical data, according to another exemplary embodiment. In FIG. 4, the exemplary embodiment described above in relation to FIG. 3 is described in more detail.

In operation 410, the medical data management apparatus 100 captures images of a user input unit of the medical diagnosis device 10. The medical data management apparatus 100 may capture images of the user input unit of the medical diagnosis device 10 by using at least one image capturing unit 120 and may obtain images corresponding to an operation of a user who manipulates the medical diagnosis device 10.

According to another exemplary embodiment, the medical data management apparatus 100 may capture images of inside an operating room where the medical diagnosis device 10 is located. Also, the medical data management apparatus 100 may capture images of an object located in the operating room.

As described above in relation to FIG. 2, the medical data management apparatus 100 may store the images captured in operation 410, as image data in the memory 150. The medical data management apparatus 100 may store time information about times when the images are captured, to be matched to the image data.

In operation 420, the medical data management apparatus 100 senses an error event. Operation 420 is similar to operation 310 of FIG. 3 and thus is not described in detail here.

In operation 430, the medical data management apparatus 100 extracts the image data corresponding to a certain period of time, from the images captured in operation 410. The medical data management apparatus 100 may extract the image data corresponding to a certain period of time before and/or after the error event is sensed in operation 420.

In operation 440, the medical data management apparatus 100 transmits information about the period of time of the extracted image data to the console device 20. Then, in operation 450, the medical data management apparatus 100 receives from the console device 20 log data matched to the period of time indicated by the information transmitted to the console device 20.

In other words, in operations 440 and 450, the medical data management apparatus 100 may receive the log data corresponding to the image data extracted with respect to the certain period of time. The medical data management apparatus 100 may obtain the image data and the log data which correspond to each other with respect to the same period of time.

In operation 460, the medical data management apparatus 100 transmits the image data and the log data to the external server 200. A detailed description thereof is similarly provided above in relation to operation 340 of FIG. 3.

Figure 5:
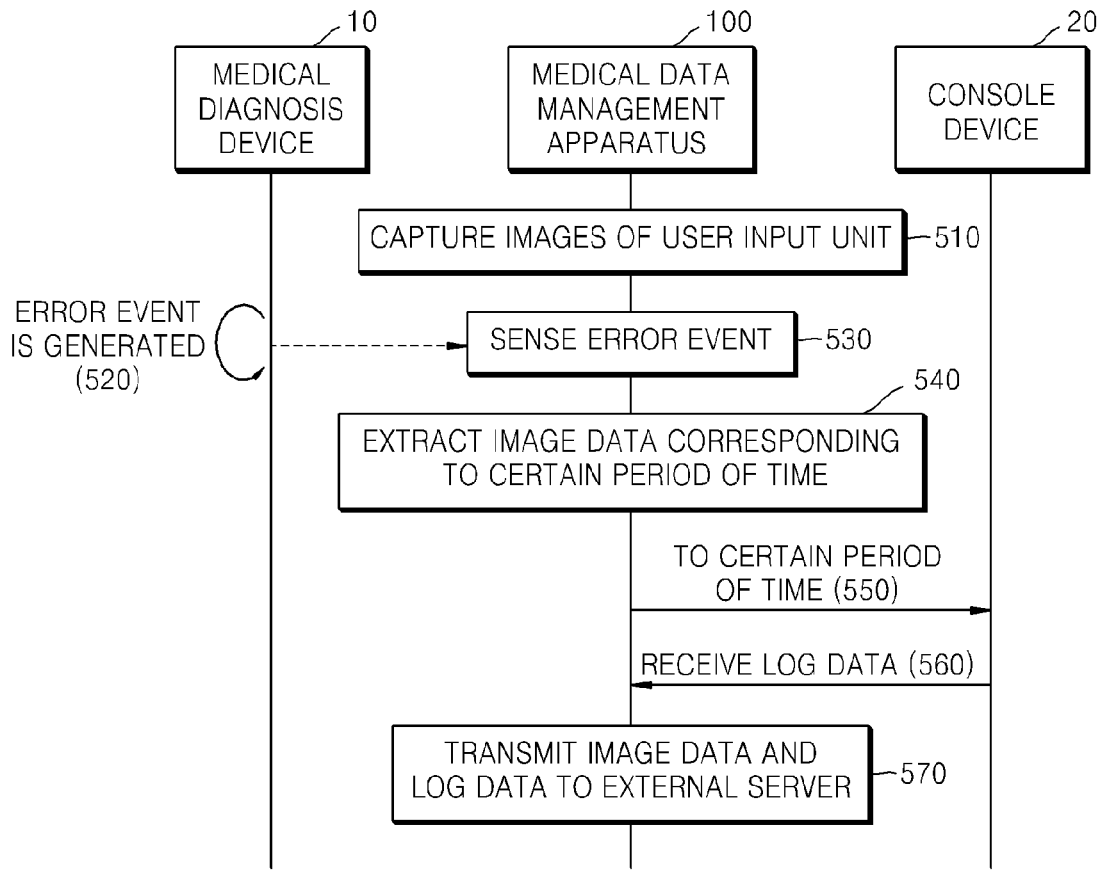
FIG. 5 is a flowchart of a method of managing medical data in a medical diagnosis system, according to an exemplary embodiment.

FIG. 5 is a flowchart of a method of managing medical data in a medical diagnosis system, according to an exemplary embodiment. In FIG. 5, detailed descriptions provided above in relation to FIGS. 3 and 4 will not be repeated here.

In operation 510, the medical data management apparatus 100 captures images of a user input unit of the medical diagnosis device 10, and generates image data. The medical data management apparatus 100 may store the image data to be matched to time information.

In operation 520, an error event is generated in the medical diagnosis device 10. In other words, the medical diagnosis device 10 may provide an unexpected result due to an incorrect manipulation by the user or a system error. The error event is described above in detail in relation to FIG. 2.

In operation 530, the medical data management apparatus 100 senses the error event of the medical diagnosis device 10. For example, the medical data management apparatus 100 may sense the error event by receiving an error event notification signal from the medical diagnosis device 10, or by analyzing the image data generated in operation 510.

In operation 540, the medical data management apparatus 100 extracts the image data corresponding to a certain period of time. The medical data management apparatus 100 may extract the image data corresponding to a certain period of time before and/or after the error event is generated.

In operation 550, the medical data management apparatus 100 may transmit to the console device 20 information about the period of time of the image data extracted in operation 540. Then, in operation 560, the medical data management apparatus 100 may receive from the console device 20 log data corresponding to the period of time indicated by the information transmitted in operation 550.

In operation 570, the medical data management apparatus 100 may transmit the extracted image data and the received log data to the external server 200.

The medical data management apparatus 100 may obtain and transmit sound data in addition to the image data and the log data. In other words, when the image data of the user input unit of the medical diagnosis device 10 is obtained in operation 510, the medical data management apparatus 100 may obtain and store sound data by recording sound in an operating room where the medical diagnosis device 10 is located.

Then, the medical data management apparatus 100 may extract sound data corresponding to the period of time of the image data extracted in operation 540, and may transmit the sound data to the external server 200 together with the image data and the log data in operation 570.

Figure 6:
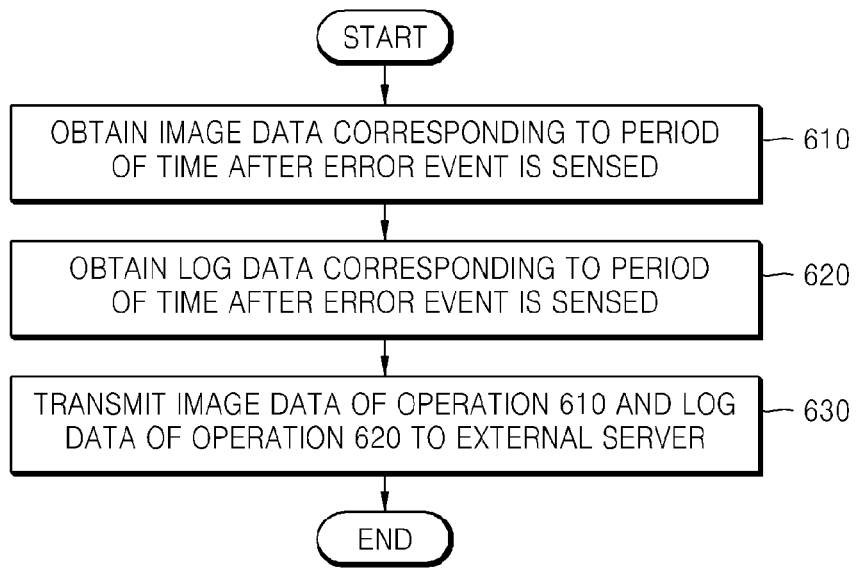
FIG. 6 is a flowchart of a method of managing medical data, according to an exemplary embodiment.

FIG. 6 is a flowchart of a method of managing medical data, according to an exemplary embodiment. In FIG. 6, a certain period of time for obtaining image data and log data after the medical data management apparatus 100 senses an error event is described.

In operation 610, the medical data management apparatus 100 obtains image data corresponding to a certain period of time after an error event is sensed. The medical data management apparatus 100 may previously determine the certain period of time according to a user input. For example, the medical data management apparatus 100 may previously set a 5 minute time period after the error event is sensed, as the period of time for obtaining the image data.

If the error event is sensed, the medical data management apparatus 100 may obtain and transmit the image data in real time. In other words, the image data corresponding to a period of time before the error event is sensed may be previously obtained. However, the image data corresponding to a period of time after the error event is sensed may not be previously obtained.

Accordingly, if the error event is sensed, the medical data management apparatus 100 may obtain and transmit the image data in real time for a predetermined certain period of time.

In operation 620, the medical data management apparatus 100 obtains log data corresponding to the certain period of time after the error event is sensed. Like operation 610, in operation 620, the medical data management apparatus 100 may obtain the log data in real time for a predetermined period of time after the error event is sensed.

In other words, the medical data management apparatus 100 may obtain and receive the log data in real time from the console device 20.

In operation 630, the medical data management apparatus 100 transmits the image data and the log data to the external server 200. In other words, the medical data management apparatus 100 may transmit to the external server 200 medical data obtained in operations 610 and 620 after the error event is sensed.

Figure 7:
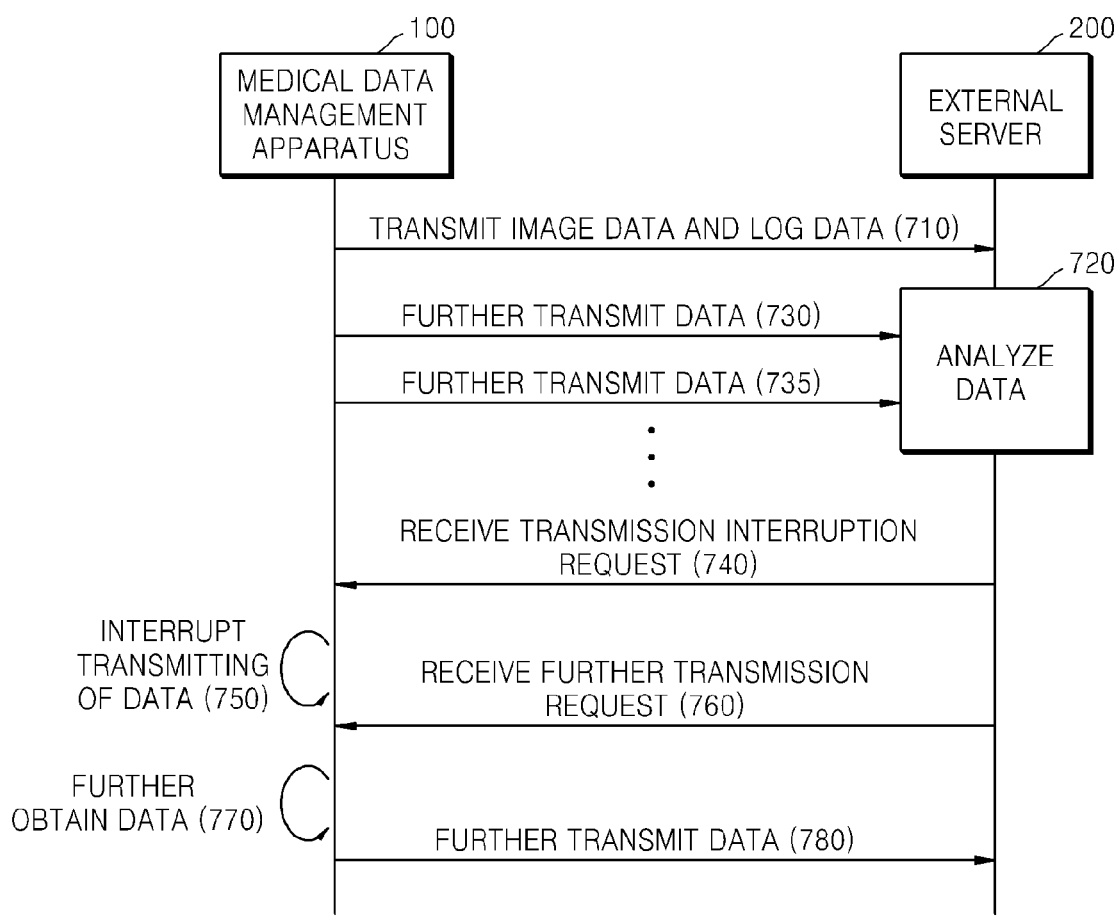
FIG. 7 is a flowchart of a method of managing medical data, according to an exemplary embodiment.

FIG. 7 is a flowchart of a method of managing medical data, according to an exemplary embodiment. In FIG. 7, communications between the medical data management apparatus 100 and the external server 200 are described.

In operation 710, the medical data management apparatus 100 transmits image data and log data to the external server 200. The medical data management apparatus 100 may transmit to the external server 200 the image data and the log data which correspond to each other with respect to a period of time before and/or an error event is sensed. As described above in relation to, for example, FIG. 2, the medical data management apparatus 100 may also transmit sound data.

In operation 720, the external server 200 analyzes the received medical data. In other words, the external server 200 may analyze the image data, the log data, and the sound data so as to check a cause and type of the error event generated in the medical diagnosis device 10.

In operations 730 and 735, the medical data management apparatus 100 further transmits the medical data to the external server 200. In other words, unlike the medical data corresponding to a period of time before the error event is sensed, the medical data management apparatus 100 may obtain and transmit the medical data in real time for a certain period of time after the error event is generated.

The medical data management apparatus 100 may obtain and transmit the medical data in units of a certain period of time. In other words, for example, the medical data management apparatus 100 may obtain the medical data for a 5 minute time period after the error event is sensed, in units of one minute, and may separately transmit the medical data to the external server 200.

During operations 730 and 735, the external server 200 may continuously analyze the medical data about the error event.

In operation 740, the medical data management apparatus 100 receives a transmission interruption request from the external server 200. In other words, the medical data management apparatus 100 may receive from the external server 200 a signal indicating that the error event has been completely analyzed, and a signal requesting to interrupt the transmitting of the medical data.

As such, in operation 750, the medical data management apparatus 100 interrupts the transmitting of the medical data. In other words, the medical data management apparatus 100 may interrupt the obtaining and transmitting of data for a certain period of time after the error event is generated.

In operation 760, the medical data management apparatus 100 receives a further transmission request from the external server 200. In other words, in order to further analyze the error event, the external server 200 may require the medical data corresponding to a period of time longer than that of the medical data that has been transmitted from the medical data management apparatus 100 or may require data from another period of time.

As such, the medical data management apparatus 100 may receive from the external server 200 the further transmission request requesting to further transmit the medical data. Then, in operation 770, the medical data management apparatus 100 further obtains the medical data. In other words, the medical data management apparatus 100 may obtain the medical data corresponding to a period of time other than those of the medical data transmitted in operations 710, 730, and 735.

In operation 780, the medical data management apparatus 100 transmits to the external server 200 the medical data further obtained in operation 770. As such, the external server 200 may perform further operations for analyzing a cause of the error event generated in the medical diagnosis device 10, and for solving the error event.

Figure 8:
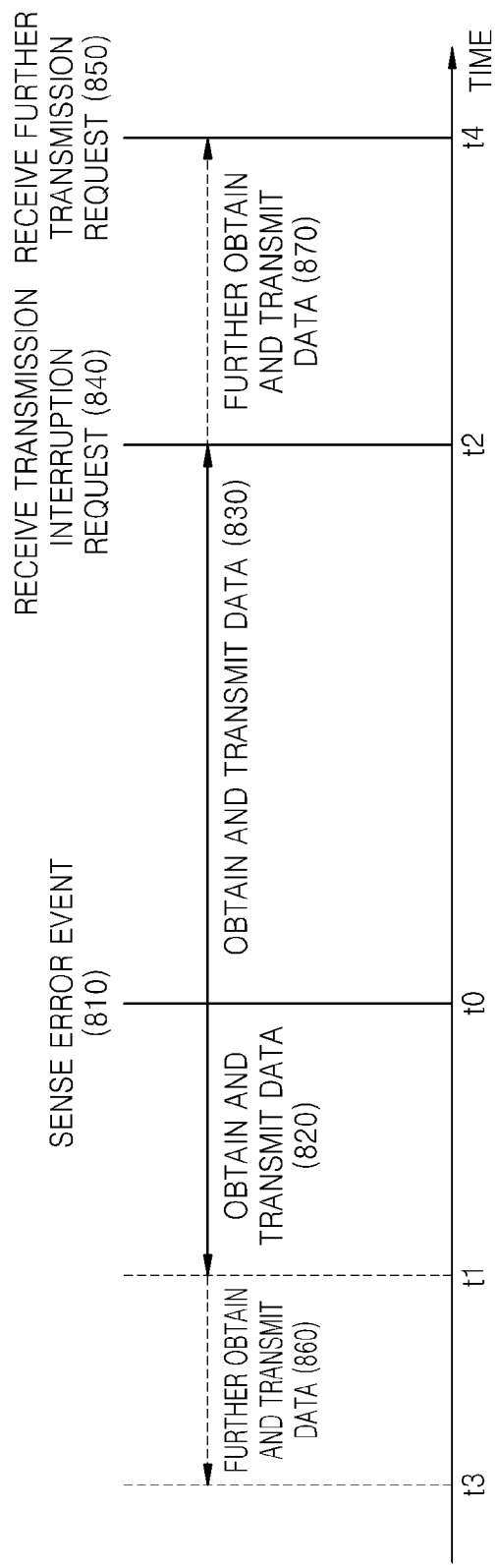
FIG. 8 is a flowchart of a method of managing medical data, according to an exemplary embodiment.

FIG. 8 is a flowchart of a method of managing medical data, according to an exemplary embodiment. FIG. 8 shows the method according to the flow of time. In FIG. 8, the descriptions provided above in relation to FIGS. 3 through 7 will not repeated here.

In operation 810, the medical data management apparatus 100 senses an error event at a point of time t0. Then, in operation 820, the medical data management apparatus 100 may obtain medical data corresponding to a period of time t1 to t0 that is a certain period of time before the point of time t0 when the error event is sensed, and may transmit the medical data to the external server 200.

Then, in operation 830, the medical data management apparatus 100 may obtain the medical data corresponding to a period of time t0 to t2 that is a certain period of time after the point of time t0 when the error event is sensed, and may transmit the medical data to the external server 200.

The medical data management apparatus 100 may obtain and transmit the medical data corresponding to the period of time t0 to t2, to the external server 200 in real time. In other words, unlike the medical data corresponding to the period of time t1 to t0, the medical data management apparatus 100 may obtain and transmit the medical data corresponding to the period of time t0 to t2, to the external server 200 in real time.

As described above in relation to FIG. 7, the medical data management apparatus 100 may obtain and transmit the medical data to the external server 200 in units of a certain period of time after the error event is generated.

In operation 840, the medical data management apparatus 100 receives a transmission interruption request from the external server 200. As such, the medical data management apparatus 100 may interrupt the obtaining and transmitting of the medical data.

In operation 850, the medical data management apparatus 100 receives a further transmission request from the external server 200. In other words, the medical data management apparatus 100 may be requested by the external server 200 to further transmit the medical data required to analyze the error event.

In operation 860, according to the further transmission request received in operation 850, the medical data management apparatus 100 obtains and transmits the medical data corresponding to a period of time t3 to t1, to the external server 200. In other words, if the medical data corresponding to the period of time t1 to t0 is not sufficient to analyze and check the error event, according to a request from the external server 200, the medical data management apparatus 100 may further manage data corresponding to a period of time before the error event is generated.

Likewise, in operation 870, the medical data management apparatus 100 further obtains and transmits the medical data corresponding to a period of time t2 to t4, to the external server 200. In other words, if the further transmission request is received at a point of time t4, the medical data management apparatus 100 may transmit the medical data obtained and stored with respect to the period of time t2 to t4, to the external server 200.

Furthermore, until the transmission interruption request is received, the medical data management apparatus 100 may obtain and transmit the medical data corresponding to a period of time after the point of time t4, to the external server 200.

Figure 9:
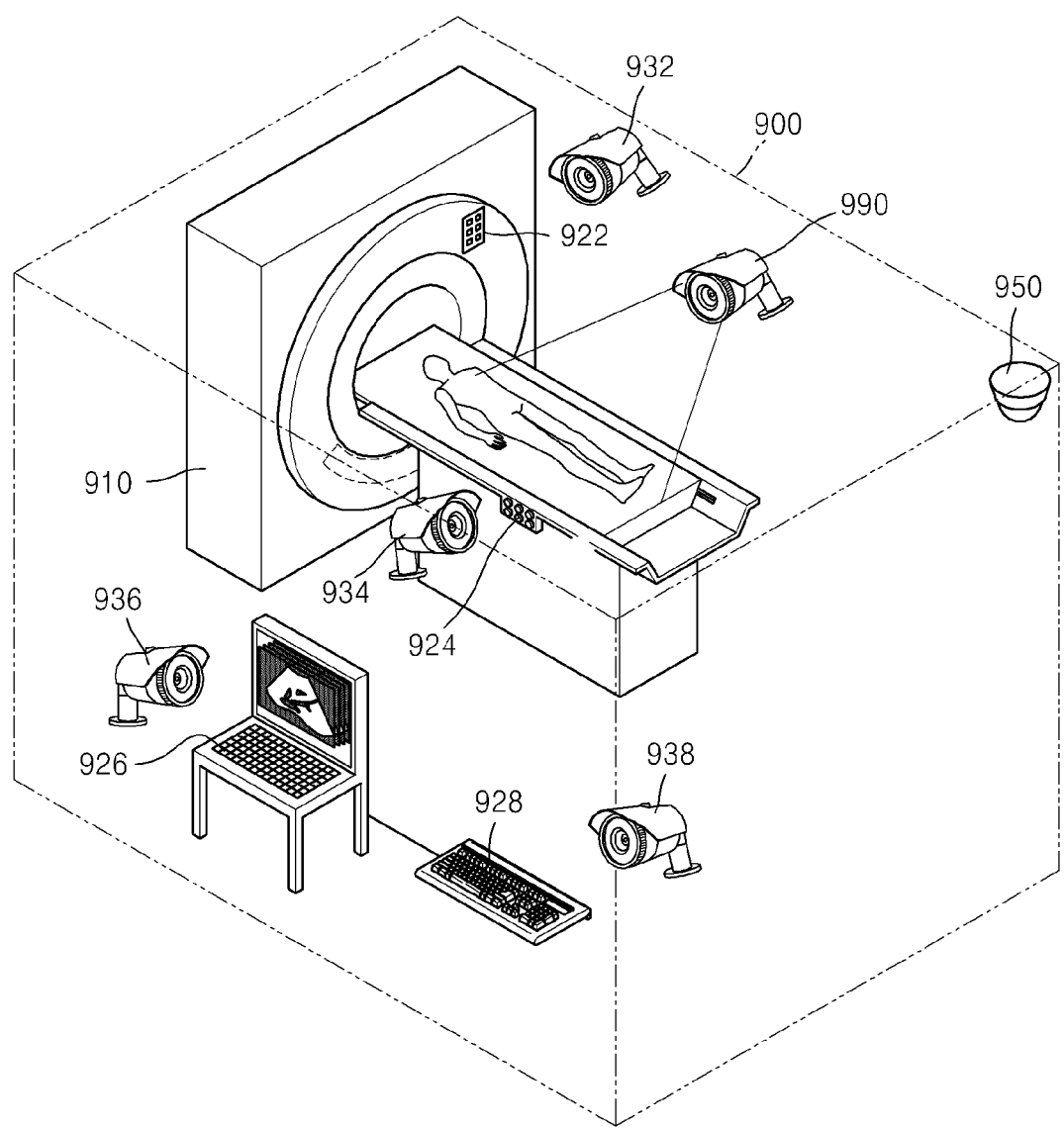
FIG. 9 is a schematic diagram showing an example of managing medical data of a computed tomography (CT) diagnosis system, according to an exemplary embodiment.

FIG. 9 is a schematic diagram showing an example of managing medical data of a CT diagnosis system, according to an exemplary embodiment. In FIG. 9, the medical data management apparatus 100 includes first through fourth image capturing units 932, 934, 936, and 938 for capturing images of a plurality of user input units included in a CT diagnosis device 910.

In other words, the medical data management apparatus 100 includes the first image capturing unit 932 for capturing images of a control panel 922 attached to a gantry of the CT diagnosis device 910. Also, the medical data management apparatus 100 includes the second image capturing unit 934 for capturing images of table control buttons 924 attached to a diagnosis table of the CT diagnosis device 910.

Likewise, the medical data management apparatus 100 includes the third image capturing unit 936 and the fourth image capturing unit 938 for capturing images of a touch panel 926 and a keyboard 928 for controlling the CT diagnosis device 910.

Also, the medical data management apparatus 100 may further include a fifth image capturing unit 950 for capturing images of inside the operating room 900. The fifth image capturing unit 950 may generate image data obtained by capturing images of inside of the while operating room 900, and thus may supplement the image data captured by the first through fourth image capturing units 932, 934, 936, and 938.

In addition, the medical data management apparatus 100 may further include a sixth image capturing unit 990 for capturing images of an object located in the operating room 900. The sixth image capturing unit 990 may capture images of the object that is being diagnosed, and may generate object image data. The medical data management apparatus 100 may transmit the object image data to the external server 200 together with the image data and log data. In addition, another image capturing unit may be located internal to touch panel 926 or another computing device and capture screenshots of the touch panel or the computing device from a memory of the computing device.

Figure 10:
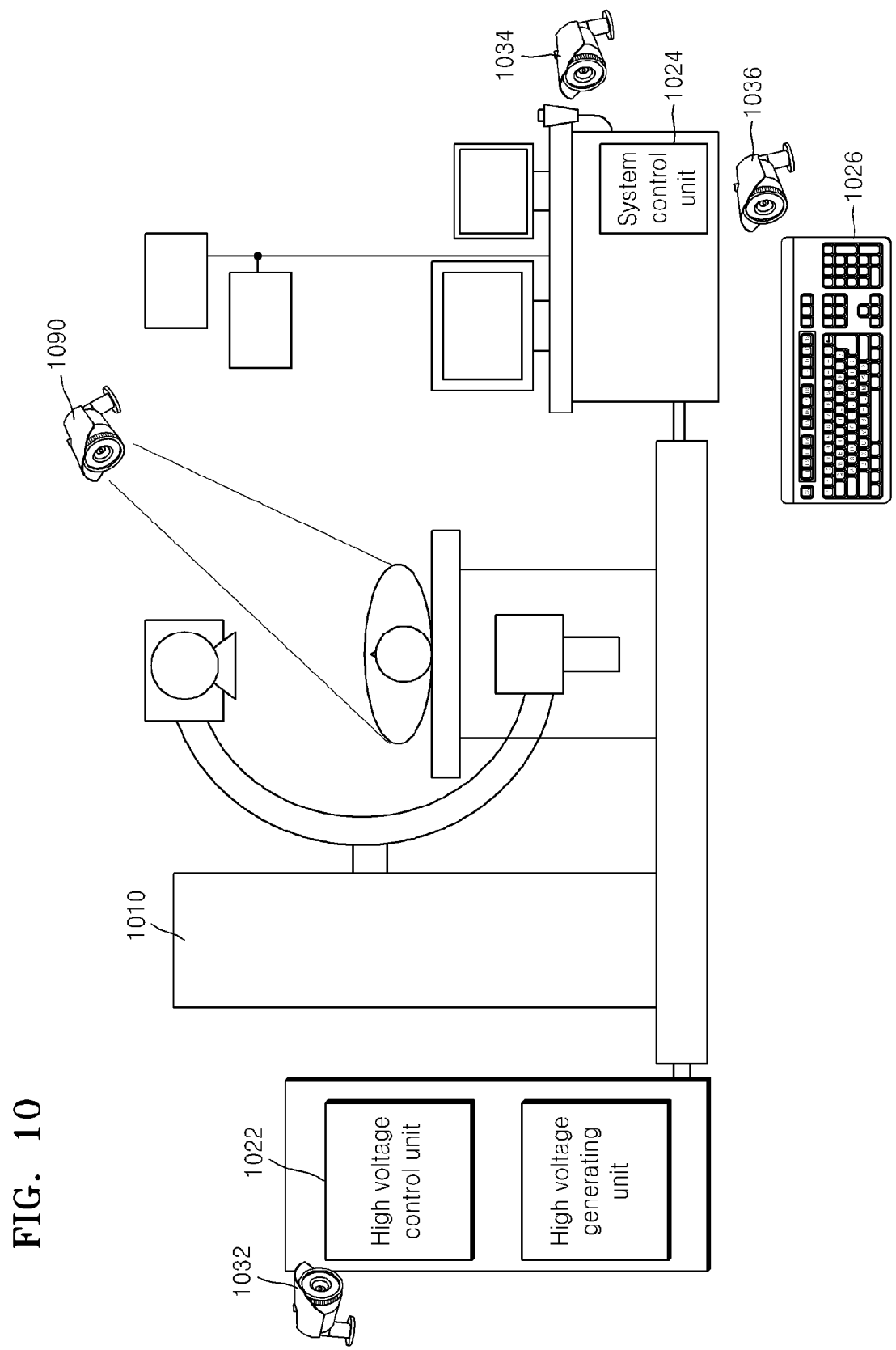
FIG. 10 is a schematic diagram showing an example of managing medical data of an X-ray diagnosis system, according to an exemplary embodiment.

FIG. 10 is a schematic diagram showing an example of managing medical data of an X-ray diagnosis system, according to an exemplary embodiment. In FIG. 10, the medical data management apparatus 100 includes first through third image capturing units 1032, 1034, and 1036 for capturing images of a plurality of user input units included in an X-ray diagnosis device 1010.

In other words, the medical data management apparatus 100 may include the first image capturing unit 1032 for capturing images of a voltage control unit 1022 of the X-ray diagnosis device 1010. Likewise, the medical data management apparatus 100 may include the second image capturing unit 1034 for capturing images of a system control unit 1024 of the X-ray diagnosis device 1010, and the third image capturing unit 1036 for capturing images of a keyboard 1026 of the X-ray diagnosis device 1010.

As described above in relation to FIG. 9, the medical data management apparatus 100 of FIG. 10 may further include an image capturing unit (not shown) for capturing images of inside an operating room where the X-ray diagnosis device 1010 is located.

Also, similarly to FIG. 9, the medical data management apparatus 100 of FIG. 10 may further include a fourth image capturing unit 1090 for capturing images of an object located in the operating room.

Figure 11:
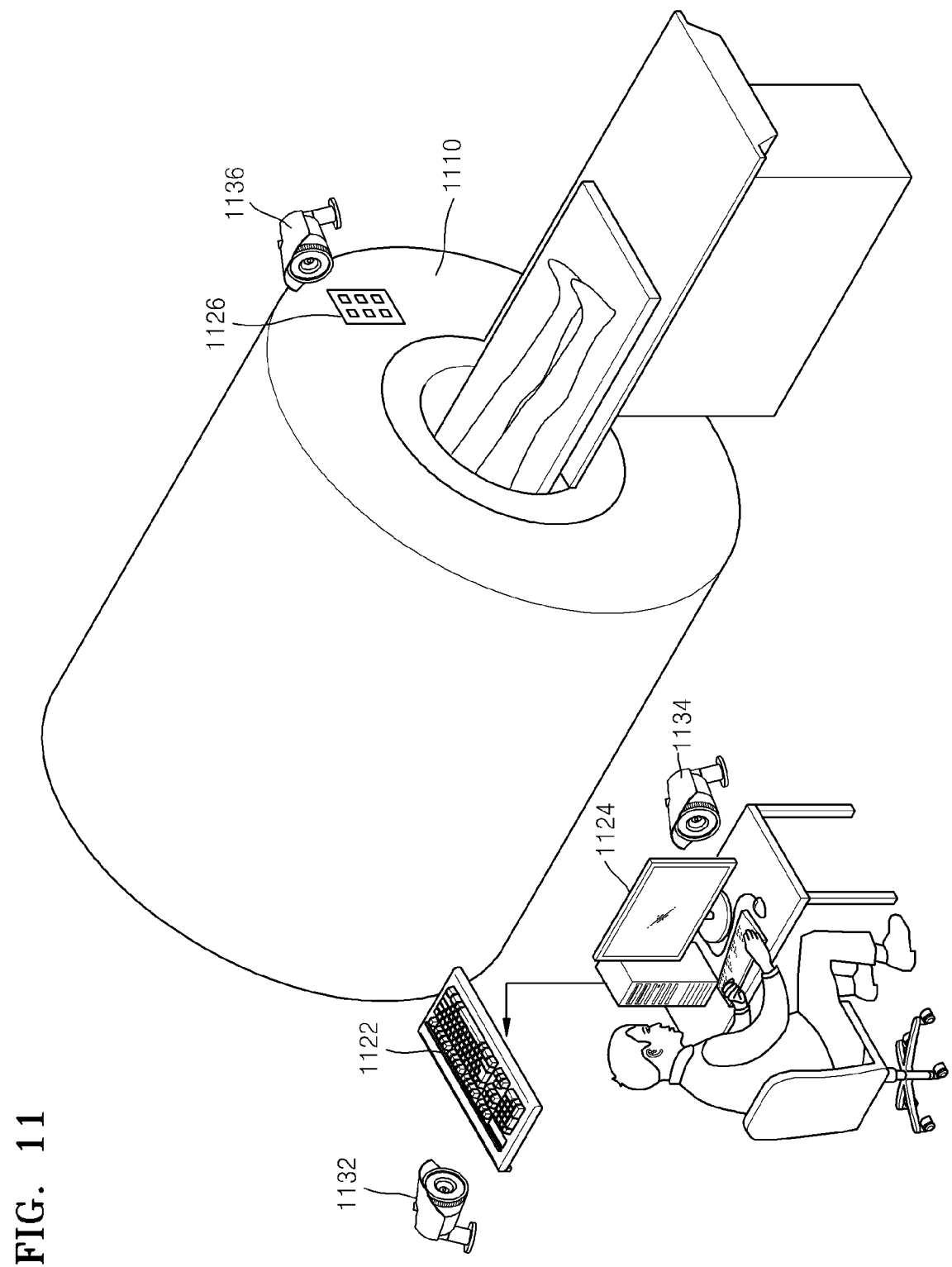
FIG. 11 is a schematic diagram showing an example of managing medical data of a magnetic resonance imaging (MRI) diagnosis system, according to an exemplary embodiment.

FIG. 11 is a schematic diagram showing an example of managing medical data of an MRI diagnosis system, according to an exemplary embodiment. In FIG. 11, the medical data management apparatus 100 may include first through third image capturing units 1132, 1134, and 1136 for capturing images of user input units of an MRI diagnosis device 1110.

The medical data management apparatus 100 may include the first image capturing unit 1136 for capturing images of a bore control panel 1126 of the MRI diagnosis device 1110. Also, the medical data management apparatus 100 may include the second image capturing unit 1134 for capturing images of a touch screen 1124 of the MRI diagnosis device 1110, and the third image capturing unit 1132 for capturing images of a keyboard 1122 of the MRI diagnosis device 1110.

Also, although not shown in FIG. 11, as described above in relation to FIGS. 9 and 10, the medical data management apparatus 100 may further include an image capturing unit for capturing images of an object diagnosed by the MRI diagnosis device 1110 in an operating room.

Figure 12:
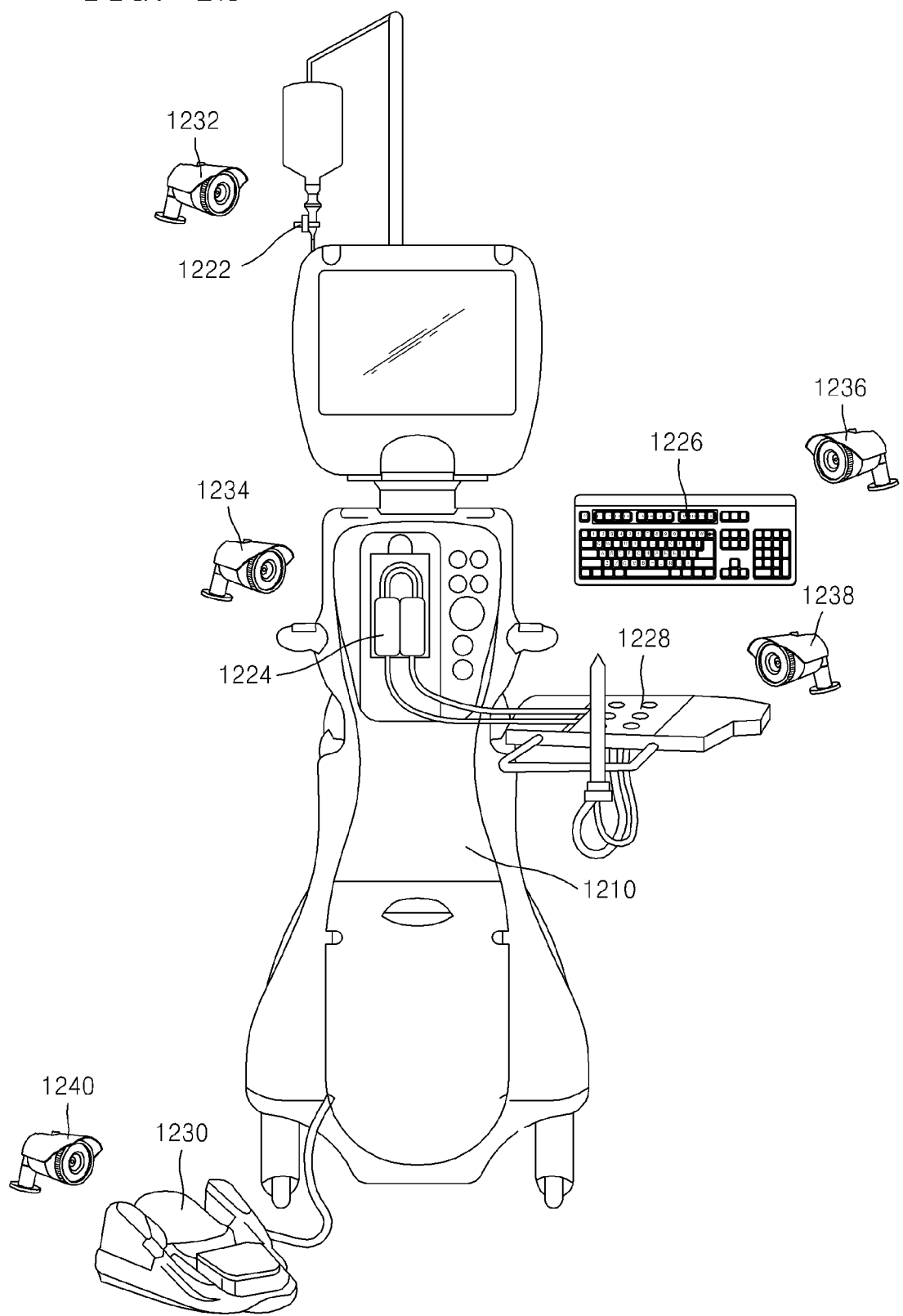
FIG. 12 is a schematic diagram showing an example of managing medical data of an ultrasound diagnosis system, according to an exemplary embodiment.

FIG. 12 is a schematic diagram showing an example of managing medical data of an ultrasound diagnosis system, according to an exemplary embodiment. In FIG. 12, the medical data management apparatus 100 may include first through fourth image capturing units 1232, 1234, 1236, 1238, and 1240 for capturing images of user input units of an ultrasound diagnosis device 1210.

The first through fourth image capturing units 1232, 1234, 1236, 1238, and 1240 may respectively capture images of a contrast medium injector 1222, a probe connector 1224, a keyboard 1226, a probe holder 1228, and a foot switch 1230 of the ultrasound diagnosis device 1210.

Similarly to FIGS. 9 and 10, in FIGS. 11 and 12, the medical data management apparatus 100 may further include an image capturing unit (not shown) for capturing images of an operating room where the MRI diagnosis device 1110 or the ultrasound diagnosis device 1210 is located.

As described above in relation to FIG. 2, the image capturing units illustrated in FIGS. 9 through 12 may be shielded from a magnetic field, an RF signal, or an X ray generated by a medical diagnosis device (e.g., 910, 1010, 1110, or 1210).

In FIGS. 9 through 12, examples of image capturing units of the medical data management apparatus 100 according to various modalities are described. However, the above descriptions are merely examples and the previous exemplary embodiments are not limited thereto.

Exemplary embodiments may be written as computer programs and may be implemented in general-use digital computers that execute the programs using a computer readable recording medium. Also, the data structure used in the exemplary embodiments described above may be recorded on a computer readable recording medium via various elements. Examples of the computer readable recording medium include magnetic storage media (e.g., ROM, floppy disks, hard disks, etc.), optical recording media (e.g., CD-ROMs, or DVDs), etc.

As described above, since the medical data management apparatus 100 obtains and transmits medical data, the external server 200 may manage the medical data for analyzing an error event of the medical diagnosis device 10. As such, a cause of the error event of the medical diagnosis device 10 may be efficiently checked. Also, a load for performing a debugging process using a debugging board may be reduced.

Also, since the medical data management apparatus 100 obtains and transmits medical data for a designated period of time, traffic consumption according to transmission of unnecessary data may be reduced.

Furthermore, since a user's manipulation is monitored and analyzed so as to give feedback on the incorrect manipulation by the user, a possibility of generating an error event may also be reduced.

While the exemplary embodiments have been particularly shown and described with reference to drawings, it will be understood by one of ordinary skill in the art that various changes in form and details may be made therein without departing from the spirit and scope of the inventive concept as defined by the following claims. The exemplary embodiments should be considered in a descriptive sense only and not for purposes of limitation. Therefore, the scope of the inventive concept is defined not by the detailed description but by the following claims, and all differences within the scope will be construed as being included in the inventive concept.

What is claimed is:

1. A method of managing medical data, performed by a medical data management apparatus, the method comprising:

sensing an error event of a medical diagnosis device;

obtaining image data by capturing images of at least one of a medical image apparatus located in an operating room, an object located in the operating room, and a user input of the medical diagnosis device with respect to a first period of time before the error event is sensed;

obtaining log data with respect to the first period of time before the error event is sensed; and storing the image data and the log data in a memory of the medical data management apparatus, wherein the medical image apparatus includes the medical diagnosis device configured to perform a medical diagnosis and a console device configured to control and manage the medical diagnosis device.

2. The method of claim 1, wherein the obtaining the log data comprises:

transmitting information about the first period of time to the console device; and receiving log data matched to the first period of time, from the console device.

3. The method of claim 1, wherein the image data and the log data correspond to each other based on the first period of time.

4. The method of claim 1, further comprising:

obtaining image data corresponding to a second period of time after the error event is sensed, from the images of at least one of the medical image apparatus and the object;

obtaining log data corresponding to the second period of time; and storing the image data corresponding to the second period of time and the log data corresponding to the second period of time in the memory.

5. The method of claim 1, further comprising:

receiving a transmission request from an external server;

obtaining further image data and further log data corresponding to a period of time according to the transmission request; and transmitting the further obtained image data and the further obtained log data to the external server.

6. The method of claim 1, further comprising obtaining sound data of the operating room with respect to the first period of time, and transmitting the image data, the log data, and the sound data.

7. The method of claim 1, wherein the sensing comprises receiving an error event notification signal from the medical diagnosis device.

8. The method of claim 1, wherein the sensing comprises executing at least one of a pattern recognition algorithm, a gesture recognition algorithm, and a color detection algorithm on the images of at least one of the medical image apparatus and the object.

9. The method of claim 8, further comprising transmitting information about one of the pattern recognition algorithm, the gesture recognition algorithm, and the color detection algorithm, the executing of which results in the error event being sensed.

10. The method of claim 1, wherein the log data comprises at least one of a history of using the console device, user information of the console device, software information of the console device, setup information of the console device, system information of the console device, and hospital information about a hospital where the medical data management apparatus is located.

11. The method of claim 1, further comprising obtaining a result of diagnosing the object as scan data with respect to the first period of time, and transmitting the image data, the log data, and the scan data.

12. The method of claim 1, further comprising:

setting an area for displaying the image data on a display; and providing the image data on the set area.

13. The method of claim 1, wherein the image data is obtained by an image capturer shielded from the medical diagnosis device.

14. The method of claim 1, wherein the image data is obtained by at least one of an ultra-high-speed camera, a wide-viewing-angle camera, and a high-definition (HD) camera.

15. A medical data management apparatus comprising:

an image capturer which is configured to capture images of at least one of a medical image apparatus located in an operating room and an object located in the operating room, and a user input of a medical diagnosis device;

at least one processor which is configured to sense an error event of the medical image apparatus, obtain image data by capturing images of at least one of the medical image apparatus and the object with respect to a first period of time before the error event is sensed, and obtain log data with respect to the first period of time before the error event is sensed; and a memory which is configured to store the obtained image data and the log data, wherein the medical image apparatus comprises the medical diagnosis device configured to perform a medical diagnosis and a console device configured to control and manage the medical diagnosis device.

16. The medical data management apparatus of claim 15, wherein the at least one processor extracts images corresponding to the first period of time, from the images of the at least one of the medical image apparatus and the object captured by the image capturer.

17. The medical data management apparatus of claim 15, wherein the at least one processor transmits information about the first period of time to a console device, and receives log data matched to the first period of time, from the console device.

18. The medical data management apparatus of claim 15, wherein the image data and the log data correspond to each other based on the first period of time.

19. The medical data management apparatus of claim 15, wherein the at least one processor obtains image data corresponding to a second period of time after the error event is sensed, from the images of at least one of the medical image apparatus and the object, and obtains log data corresponding to the second period of time, and wherein the medical data management apparatus further comprises a communicator which is configured to transmit the image data corresponding to the second period of time and the log data corresponding to the second period of time, to an external server.

20. The medical data management apparatus of claim 15, further comprising a communicator which is configured to receive a transmission request from an external server, wherein the at least one processor obtains further image data corresponding to a period of time according to the transmission request, and further log data corresponding to the period of time according to the transmission request, and wherein the communicator transmits the further obtained image data and the further obtained log data to the external server.

21. The medical data management apparatus of claim 15, wherein the at least one processor is further configured to obtain sound data of the operating room where the medical image apparatus is located, with respect to the first period of time, wherein the medical data management apparatus further comprises a communicator which is configured to transmit the image data, the log data, and the sound data to an external server.

22. The medical data management apparatus of claim 15, wherein the at least one processor receives an error event notification signal from the medical image apparatus.

23. The medical data management apparatus of claim 15, wherein the at least one processor executes at least one of a pattern recognition algorithm, a gesture recognition algorithm, and a color detection algorithm on the captured images.

24. The medical data management apparatus of claim 23, further comprising a communicator which is configured to transmit information about one of the pattern recognition algorithm, the gesture recognition algorithm, and the color detection algorithm, which has sensed the error event.

25. The medical data management apparatus of claim 15, wherein the log data comprises at least one of a history of using the console device, user information of the console device, software information of the console device, setup information of the console device, system information of the console device, and hospital information about a hospital where the medical data management apparatus is located.

26. The medical data management apparatus of claim 15, further comprising a communicator which is configured to obtain a result of diagnosing an object as scan data with respect to the first period of time, and transmits the image data, the log data, and the scan data.

27. The medical data management apparatus of claim 15, further comprising:
a display,
wherein the at least one processor is further configured to set an area for displaying the image data on the display, and provide the image data on the set area.

28. The medical data management apparatus of claim 15, wherein the image capturer obtains the image data while being shielded from the medical diagnosis device.

29. The medical data management apparatus of claim 15, wherein the image capturer comprises at least one of an ultra-high-speed camera, a wide-viewing-angle camera, and a high-definition (HD) camera.

30. A non-transitory computer-readable recording medium having recorded thereon a computer program for executing the method of claim 1.

* * * * *